United States Patent [19]
Farnsworth et al.

[11] Patent Number: 5,922,608
[45] Date of Patent: Jul. 13, 1999

[54] MACROMOLECULE SEQUENCING PACKET AND METHOD OF USE

[75] Inventors: Vincent R. Farnsworth, Agoura; Wulf L. Carson, San Dimas, both of Calif.

[73] Assignee: Beckman Instruments, Inc., Fullerton, Calif.

[21] Appl. No.: 08/690,667

[22] Filed: Jul. 31, 1996

[51] Int. Cl.⁶ .................................................. G01N 33/545
[52] U.S. Cl. ............................... 436/89; 436/178; 435/6; 428/64.1; 428/405; 428/406; 428/407
[58] Field of Search ....................... 436/85, 89, 177–178; 435/6; 428/64.1, 403–407, 429, 447

[56] References Cited

U.S. PATENT DOCUMENTS 4,631,211  12/1986  Houghten .
5,137,765  8/1992  Farnsworth .

OTHER PUBLICATIONS

System 6300/Gold High Performance Amino Acid Analyzers Price List, Beckman Instruments, Inc., Sep. 1993.
Productivity Multiplies with TriCart, Beckman Instruments, Inc., 1992.
TriCart Productivity Comparison, Beckman Instruments, inc., 1993.
Brochure entitled *The LF 3000 Protein Sequencer*, Beckman Instruments, Inc., 1993.

*Primary Examiner*—Lyle A. Alexander
*Attorney, Agent, or Firm*—William H. May; Margaret A. Kivinski; Loeb & Loeb

[57] ABSTRACT

A method, apparatus and article for sequencing polypeptides and proteins ("macromolecules") utilizes a sequencing packet comprised of a plurality of substrates having two different derivatization chemistries within a forarninous container. The sequencing packet is disposed within a reaction chamber in a cartridge assembly having an inlet and outlet. An unknown target macromolecule, and preferably a control macromolecule are bonded to the substrates. The macromolecule and control are then simultaneously sequenced. The control serves to monitor the efficacy of the sequencing process.

18 Claims, 6 Drawing Sheets

MACROMOLECULE SEQUENCING PACKET AND METHOD OF USE

BACKGROUND

This invention is directed to sequencing of polypeptides and proteins.

Biotechnologists have identified proteins in animal, plant and microorganism cells that combat or prevent disease, confer resistance to plants for insects, improve the taste, appearance and shelf life of agricultural products, prevent fouling of hulls of boats, and can be used to clean soiled clothing. These proteins are made of amino acids linked together. There are 20 commonly occurring amino acids. The order in which the amino acids are linked together is known as the primary structure of the protein. A short chain of amino acids is called a polypeptide.

Once a protein is identified, it can be mass produced and put to constructive use. To do this, the protein needs to be sequenced, i.e., determine which amino acids constitute the protein and in what order they are linked together. The sequence data is then used in conjunction with the genetic code to prepare probes to find the gene within the cell which codes for that protein. Once the gene is identified, it can be cloned into a suitable host cell for expressing the gene and producing the protein.

Sequencing of proteins can also be useful for gene therapy or alteration. In gene therapy or alteration, a protein of interest is identified within a cell. The protein is then sequenced, and the sequence information is used in conjunction with the genetic code to make probes to identify the gene which codes for the protein. Once the gene is identified, it may be possible to manipulate that gene in an animal or plant to turn it "on" or "off", replace it with another gene, or transfer it to another animal or plant.

The process of sequencing a macromolecule such as a protein or polypeptide has been automated. There are two basic approaches for manipulating a macromolecule in the automated sequencing operation. One approach is to bond the macromolecule to a substrate such as support beads and pack the support beads into a column. This approach suffers from the disadvantage that the support beads can swell or become fouled, resulting in the column becoming plugged. Also, the beads can shrink resulting in undesirable channeling.

The second sequencing process is to bond the macromolecule to a substrate such as filter paper or polymeric membranes. This approach suffers from the disadvantage of the lack of any built-in system for determining the accuracy of the sequencing technique. There is no mechanism available to determine if the sequencing process is performing properly while actually doing the sequencing.

Accordingly, there is a need for a sequencing process which overcomes problems related to bead shrinkage, bead swelling, and column plugging; and includes a built-in system for determining the accuracy of the sequencing results.

SUMMARY

A sequencing method according to the present invention utilizes a sequencing packet that comprises a foraminous container containing a plurality of substrates. The substrates are larger than any of the foramen of the container so that they do not leak out of the container. At least some of the substrates have attached thereto a sample macromolecule, namely a polypeptide or protein whose sequence is to be determined. The substrates and the container are insoluble in water. The sample macromolecule in the packet is subjected to a degradation reaction to cleave a terminal unit from the sample macromolecule. The cleaved terminal units are then analyzed.

By repeating degradation of the sample macromolecule and analyzing the cleaved units, the sequence of the sample macromolecule is determined.

Typically the sample macromolecules are attached to the substrates by derivatizing the substrates. Typical substrates that can be used are glass, controlled pore glass, and polypropylene.

In a preferred version of the invention, the sequencing packet also contains a control macromolecule, the sequence of the control macromolecule being known. The control macromolecule can be attached to the same substrate as used for the sample macromolecule, or to a different substrate. The same or different derivitizations can be used for bonding the sample and control to the substrate. When different substrates are used, they can be substantially permanently joined together, or fused together through a carrier.

The sequencing packet can be provided to the user with or without a control macromolecule. When no control macromolecule is provided, the user of the sequencing packet can add a selected control macromolecule to the sequencing packet, where the packet contains a substrate derivatized for attachment of the control.

In the version of the invention where a control is utilized, the sample macromolecule and the control are simultaneously subjected to the degradation reaction to cleave at least one terminal unit from both macromolecules. The cleaved units are analyzed, and the cleaved units are compared against the known sequence of the control macromolecule to make certain that the cleaving and analysis are being performed correctly.

The present invention also includes an apparatus for sequencing the sample macromolecule. The apparatus comprises a housing and at least one sequencing packet, and preferably a plurality of stacked sequencing packets, removably contained in the housing. The housing has an inlet for introducing the degradation reagents for cleavage of terminal units from the sample macromolecule, and an outlet for withdrawal of cleaved terminal units.

By use of the sequencing packets, problems related to bead shrinkage and swelling, and column plugging are avoided. Moreover, by use of the control, the sequencing method of the present invention provides a built-in system for determining the accuracy of the sequencing results.

BRIEF DESCRIPTION OF THE DRAWINGS

These and other features, aspects and advantages of the present invention will become better understood from the accompanying drawings, description and appended claims where:

DETAILED DESCRIPTION OF THE INVENTION

Figure 1:
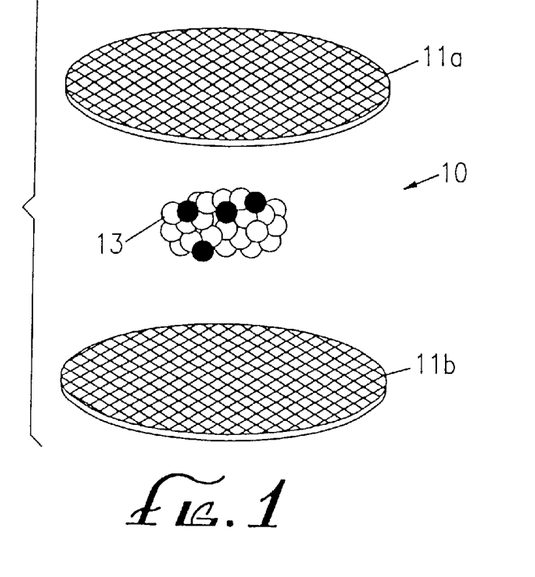
FIG. 1 is an exploded perspective view of a sequencing packet according to the present invention.
Figure 2:
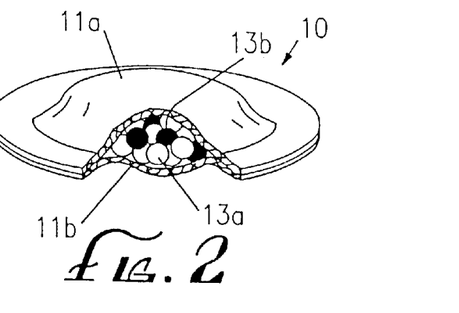
FIG. 2 is a perspective view, partially cut away, of the sequencing packet illustrated in FIG. 1.

This invention is directed to a method and article for sequencing a polypeptide or protein. Referring to FIGS. 1 and 2, a sequencing packet or container 10 is made of two sheets 11A and 11B of foraminous material. The packet 10 contains a plurality of substrates, which can be beads 13A. Bead substrates 13A are derivatized for attachment of a sample macromolecule, also referred to as a "target macromolecule." Optionally, the packet 10 contains substrates 13B derivatized for attachment of a control macromolecule. Substrates 13A and 13B can be the same or different, and the derivatization for bonding sample macromolecule and the control macromolecule to the substrates can be the same or different. When the beads 13A and 13B are the same, i.e. are the same material, same size, same configuration, and same composition, and have the same derivatization, there is effectively only one type of bead substrate 13 which is used for attachment of both sample and control macromolecule.

The sample macromolecule to be sequenced is attached to the substrate 13A in the sequencing packet 10. Likewise the control macromolecule is attached to the substrate 13B in the sequencing packet 10.

Figure 3:
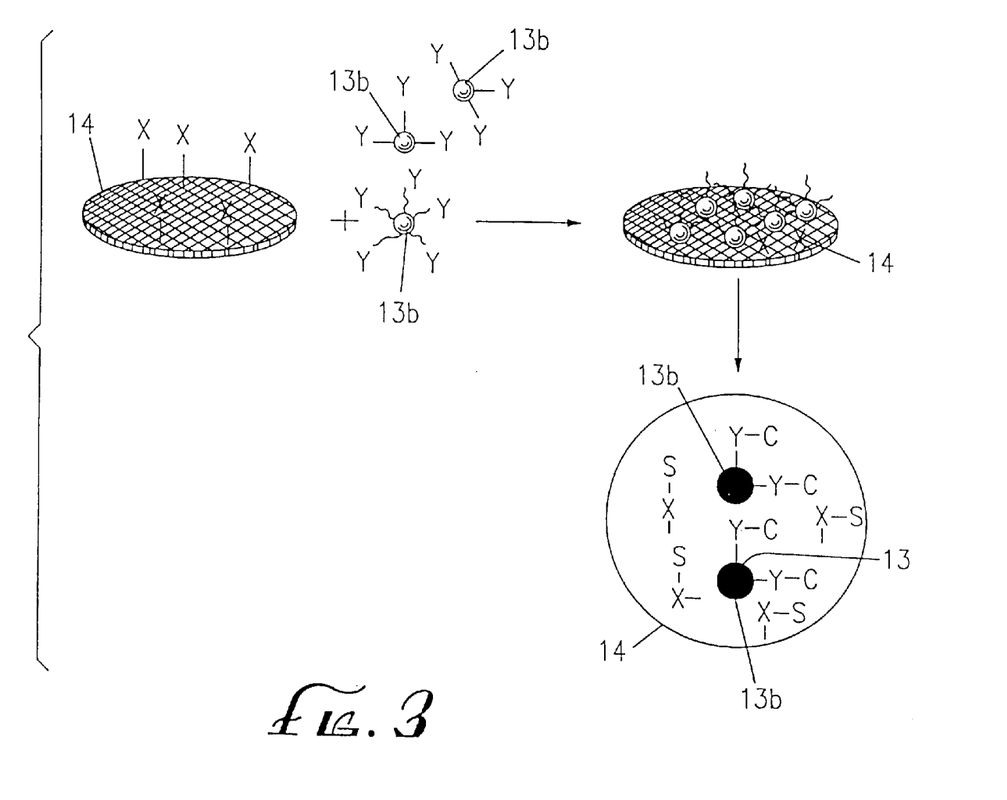
FIG. 3 is a perspective view of a substrate suitable for use in a sequencing packet.

With reference to FIG. 3, substrates can have other shapes, such as a disc shape 14. The disc shaped substrate 14 is derivatized with "X" attachment groups for attachment of sample macromolecules "S". Bead shaped substrates 13B are derivatized with "Y" attachment groups for attachment of control macromolecule "C.

Packet Material—As shown in FIGS. 1 and 2, the packet 10 is typically made from sheet material 11a and 11b; however, other forms of material are usable in embodiments of the invention. For example, the material can be in tube form or plate form. The packet material is insoluble in water and does not react with or adversely affect the sequencing chemicals that are being employed.

The sheets 11a and 11b are foraminous. The foramen are achieved through pores or through a woven or non-woven fabric that has the effect of pores. The term "effective pore size" refers to the size of particle that can flow through a material as if it had pores. The effective pore size of the packet material is from about 5 microns to about 50 microns, and the preferred effective pore size is about 10 microns. An effective pore size greater than about 5 microns is needed for good flow of sample and sequencing chemicals through the packet material, and a pore size smaller than about 50 microns is needed to keep substrates to be contained within the packet from escaping.

The packet material can be polypropylene, polyethylene, polystyrene, vinyls, glass and mixtures of the foregoing. A preferred material is woven polypropylene cloth. A most preferred material is polypropylene depth filters. Depth filters are commercially available from Gelman Services, 600 South Wagner Road, Ann Arbor, Mich. 48106 as part number G1720, 10 micron filter.

The thickness of the container material is such that it is sufficiently flexible that two sheets can be drawn together around a plurality of substrates and allow for the movement of the substrates within the container. Plastic sheets and glass fabric meet this flexibility requirement when the thickness of the packet material is from about 0.5 millimeters to about 1.5 millimeters, with a preferred thickness of about 1 millimeter. Such a thickness provides appropriate material strength without undue consumption of material.

Container construction—The packet 10 can have a square or disk (circular) shape cross-sections. Other geometries are usable, but less preferred. For example, the container can have a cross-section that is triangular, pentagonal, hexagonal or other shapes. Referring to FIG. 1, the packet container 10 is usually constructed by cutting approximately matching first and second sheets 11a and 11b in a circular shape, a plurality of substrates 13 are disposed between the sheets 11a and 11b, and the edges of the two sheets are attached together via heat fusion, sewing, adhesives or solvent fusion.

An alternative method to construct the packet 10 is to make it out of a single sheet of material cut into an approximately symmetrical shape. The sheet is folded over along the axis of symmetry and the open edges of the perimeter are attached together. Another alternative method to construct the packet 10 is to use a tube material. The tube is loaded with substrate and the ends sealed as described above.

The packet 10 is sufficiently large to accommodate from about 1 milligram to about 15 milligrams of substrate, and preferably about 5 to 7 milligrams. For a packet having a circular cross-section, the diameter of the packet is typically from about 5 to about 15 millimeters with a preferred diameter of about 8 millimeters. For a square shaped packet, the length of each side is from about 5 millimeters to about 15 millimeters with a preferred length of about 8 millimeters.

Substrate and derivatization of substrate for bonding macromolecule and control—The substrate is insoluble in water and does not react with or adversely effect the sequencing chemicals. Although the substrate is usually beads (ie., spherical) or disc-shaped, other shapes are usable, for example, squares, pentagons and pyramids. Beads are preferred over disks and other shapes because beads provide maximum surface area per unit volume. This in turn results in a greater load of sample or control macromolecule per unit of volume.

Preferred bead substrates 13 have a diameter of from about 50 microns to about 150 microns, with a preferred diameter of about 75 microns. In terms of mesh size, the beads are larger than about 200 mesh and smaller than about 400 mesh, with a preferred size being about 400 mesh.

The substrate is capable of being derivatized for attachment of sample or control macromolecule. The attachment can be accomplished by hydrophobic, ionic or covalent bonding. Ionic bonding of a polypeptide to a substrate can be effected by treating the substrate with a bonding agent to add positive or negative charges. Disclosed in U.S. Pat. No. 5,135,785, which is incorporated herein by reference, is a method for the ionic, non-covalent bonding of a macromolecule by derivatization of glass with a silica-binding substance bearing a negative charge, specifically a sulfonic acid group. This treatment results in $SO_3^-$ and $NH_4^+$ groups on the surface for ionic interaction with the sample or control macromolecule. The substrate can be derivatized with 2-(4-chlorosulfonyl phenyl) ethyl trimethoxysilane. The peptide sequencing performance is improved if the support is also derivatized with a monomeric silica-binding substance bearing a free quaternary ammonia group, such as N-trimethoxysilyl propyl - N, N, N-trimethyl ammonium chloride. This treatment results in positively charged quaternary amine groups, which in turn bind to linking groups of the carboxy tenninus of the polypeptide to be sequenced.

A method for bonding polypeptides to polystyrene or glass by either covalent linkages or absorption is taught in U.S. Pat. No. 4,065,412 to Dreyer. A method for embedding a macromolecule or control in a permeable solid matrix formed as a thin film on a support such as a glass fiber sheet is taught in U.S. Pat. Nos. 4,704,256 and 4,603,114 to Hood. These patents teach that the matrix is preferably a polymeric quaternary ammonium salt, since the positively charged quaternary ammonium groups interact strongly with the negatively charged glass surface. A method for bonding polypeptides to glass using silanes is disclosed in U.S. Pat. No. 3,652,761. Methods for covalently bonding a polypeptide to polystyrene, aminated polystyrene, carboxylated polystyrene or polyvinyl chloride using as a coupling agent dialdehydes, unsaturated aldehydes is disclosed in U.S. Pat. No. 4,695,537 to Dorsett. Dorsett also discloses bonding polypeptides to cyanogen bromide activated agarose. All of these patents are incorporated herein by reference.

Methods for hydrophobic bonding of a macromolecule to a substrate are described in Southan, *Techniques in Protein Chemistry III*, Ed., Hogue-Angelletti, Academic Press, N.Y., 1992, p. 69. A preferred method of hydrophobic bonding uses an eighteen carboxy alkane-substituted bead-shaped substrate. Typically, about 50 to about 500 picomoles of sample macromolecule or control macromolecule dissolved in about 20 microliters to about 30 microliters of 20% acetonitrile is dried onto the bead-shaped substrate having a diameter of about 75 microns. The substrates are made out of polystyrene, substituted polystyrene, latexes, polyacrylamides, polyamides, polyvinylchloride, polypropylene, agarose, cellulose, glass and controlled pore glass. The preferred materials for substrate are controlled pore glass and polypropylene.

Referring to FIG. 1, when the same derivatization is used for the control and the sample, care is used when bonding sample macromolecule and control macromolecule to the substrate so that both sample and control bond to the substrate, and not just control or sample.

Referring to FIG. 3, an integrated derivatized substrate is made by taking two substrates 13 and 14 having different derivatization chemistries. These substrates are then fused together to form a single integral unit with the result being a single surface with two different derivatization chemistries. The fusion is accomplished by either heat fusion, solvent fusion or adhesives. Alternatively, two substrates having different derivatization chemistries can be fused to a common carrier. The carrier is any material which itself could be a substrate, preferably, glass fibers or polypropylene.

Advantages of an integrated derivatized substrate include the ability to have varied configurations of support and reactive surfaces for custom sequencing and to reduce chemical background noise. For example, by integrating a substrate with a desired reactive group into polypropylene, it is possible to have polypropylene as the substrate even when it is difficult to attach the reactive group to polypropylene. Also, reactive groups are easily quantitated before integration into the surface.

Packet housings and reaction chamber—Sequencing packets can be conveniently placed in a reaction chamber, individually or stacked on top of each other. Reaction chambers commonly used in protein sequencing instruments are suitable for housing sequencing packets described herein. A particularly preferred housing is the reaction cartridge supplied with the LF 3000 available from Beckman Instruments. The Beckman Instrument LF 3000 cartridge is capable of housing the sequencing packets described herein and includes an inlet for allowing sequencing reagents to come into contact with the sequencing packet and an outlet for releasing reagents and cleaved reaction products.

Figure 4A:
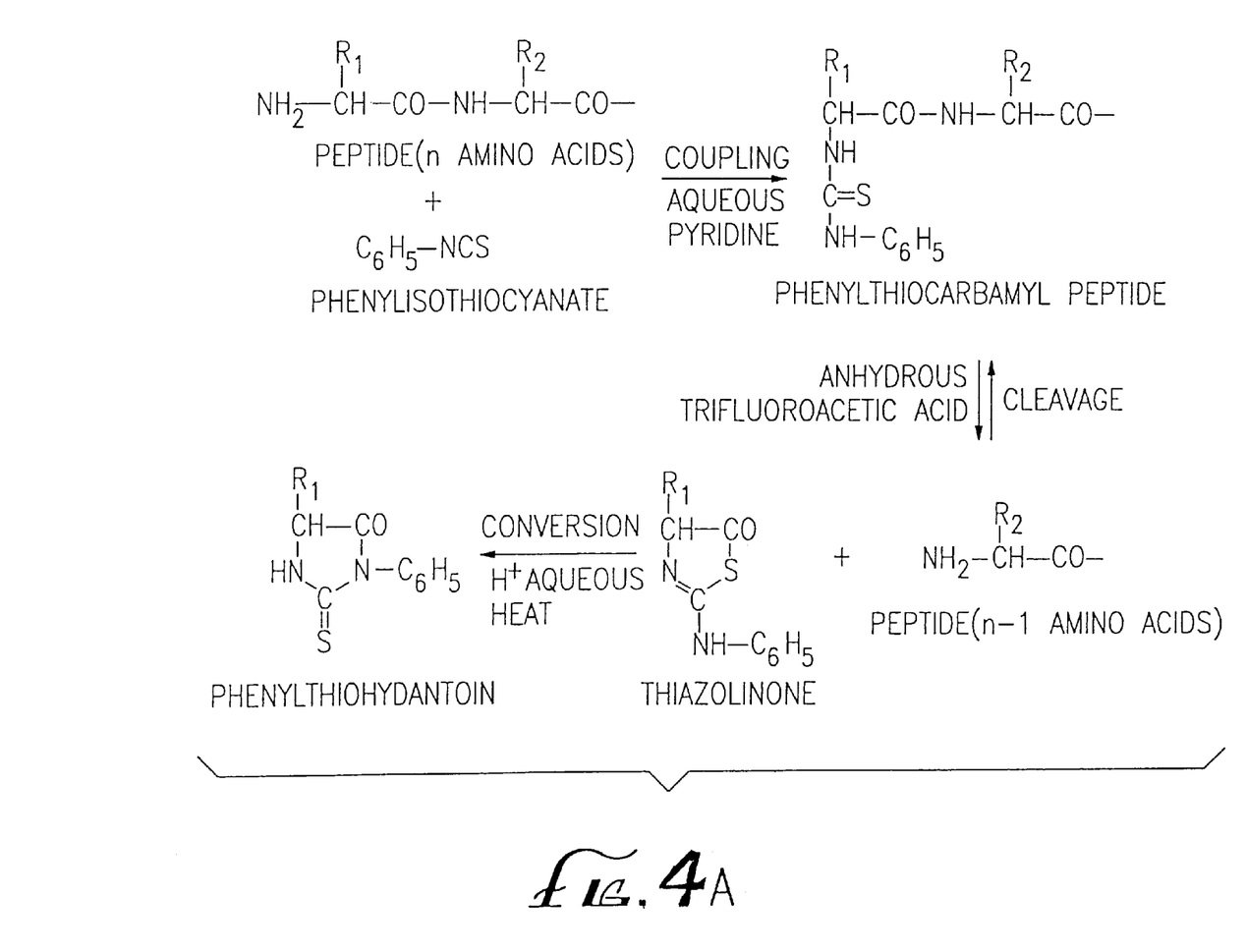
FIGS. 4A and 4B are flow charts showing the steps in sequencing a polypeptide or protein using amino terminus (Edman) degradation and carboxy terminus (Bailey & Shively) degradation respectively.
Figure 4B:
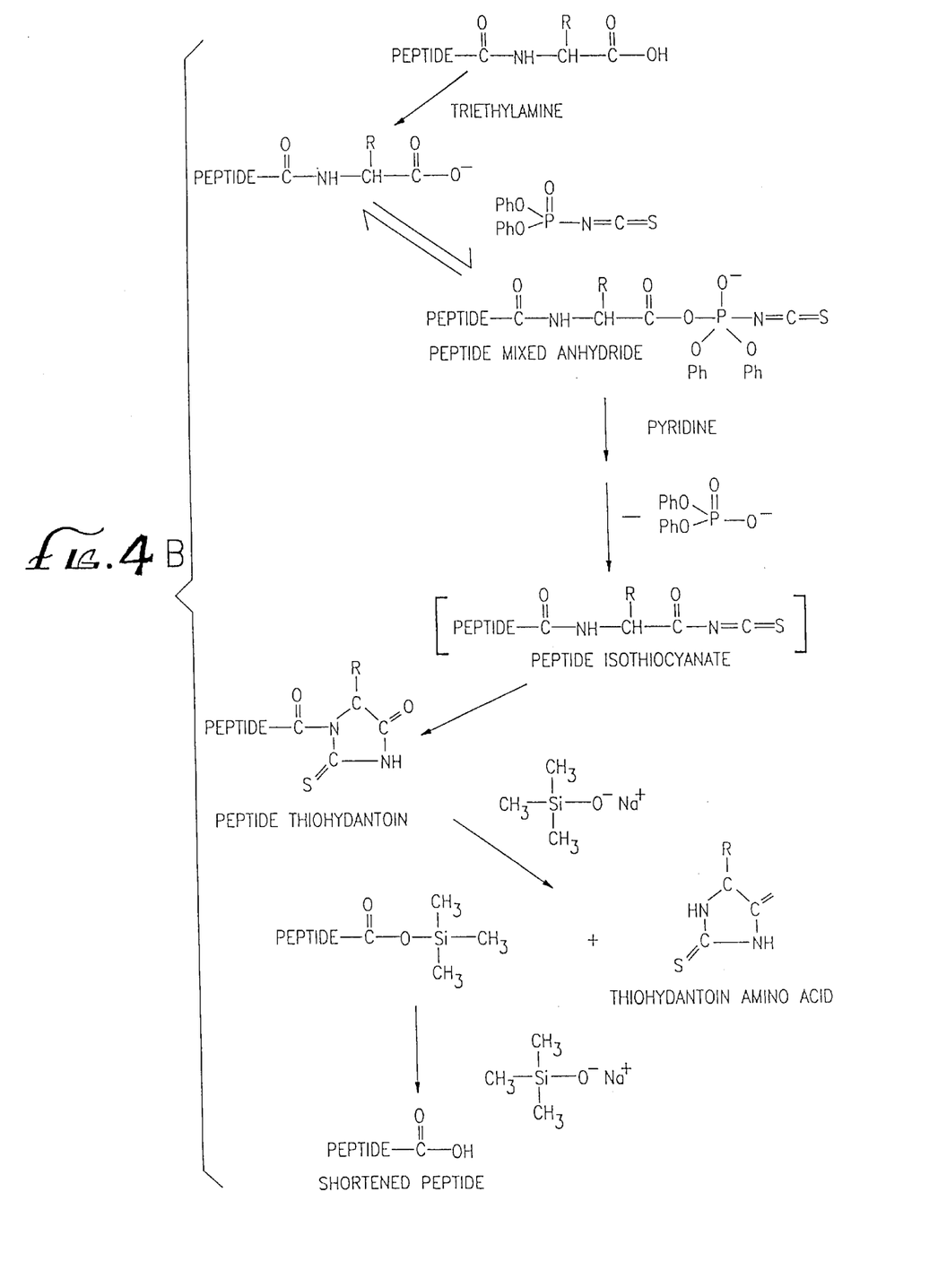
Figure 5A:
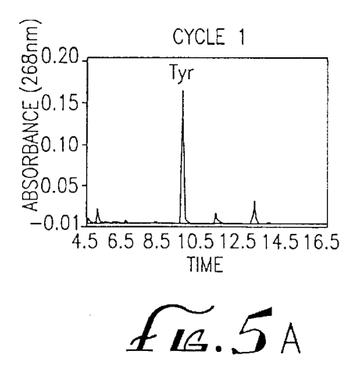
FIGS. 5A–5Q show analytical chromatograms for the sequencing of Dynorphin A according to the present invention.
Figure 5B:
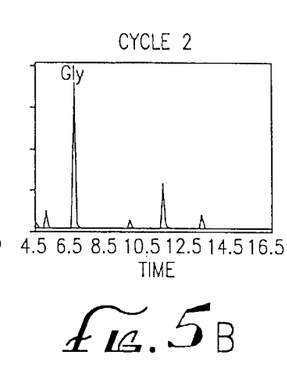
Figure 5C:
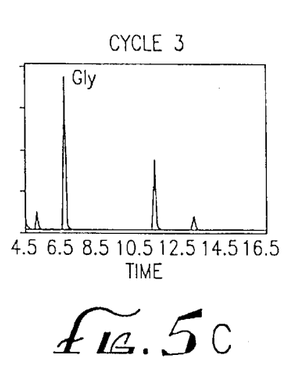
Figure 5D:
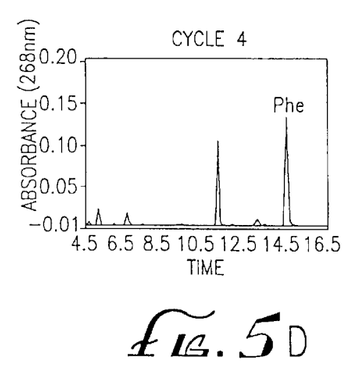
Figure 5E:
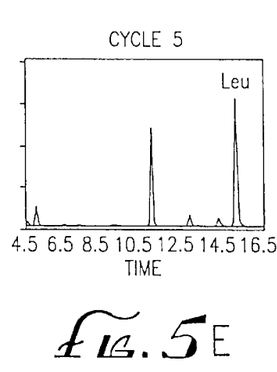
Figure 5F:
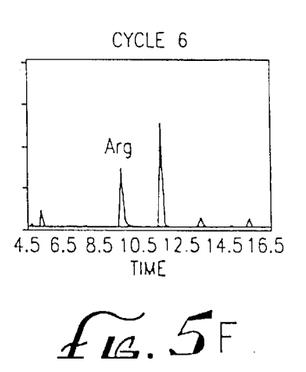
Figure 5G:
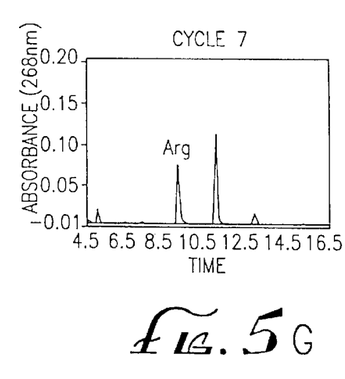
Figure 5H:
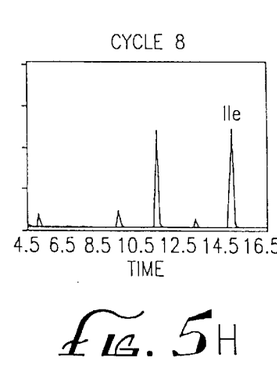
Figure 5I:
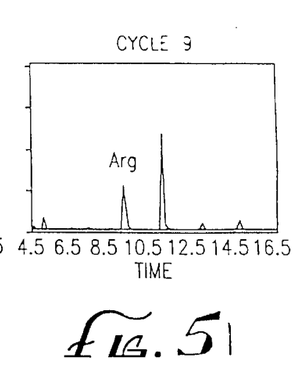
Figure 5J:
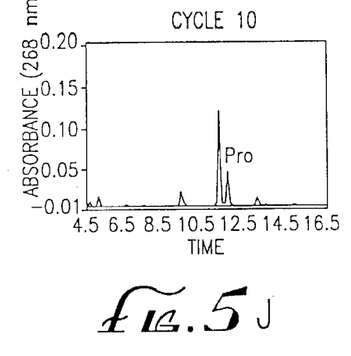
Figure 5K:
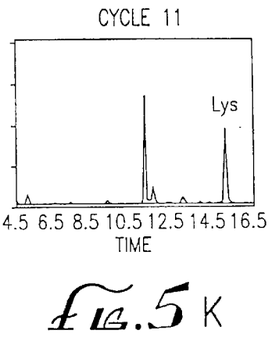
Figure 5L:
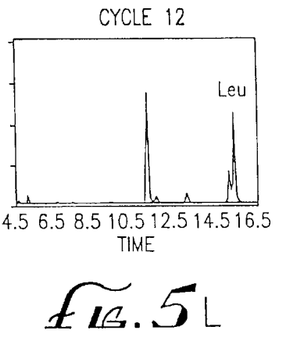
Figure 5M:
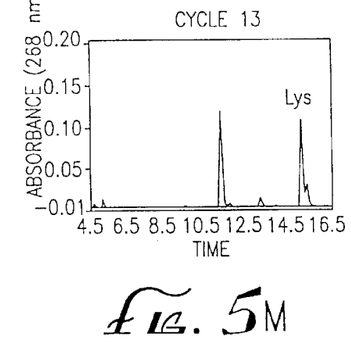
Figure 5N:
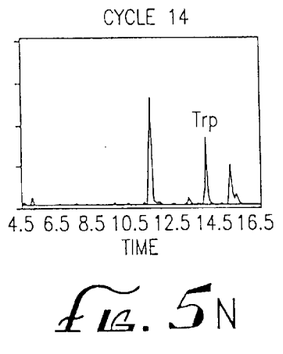
Figure 5O:
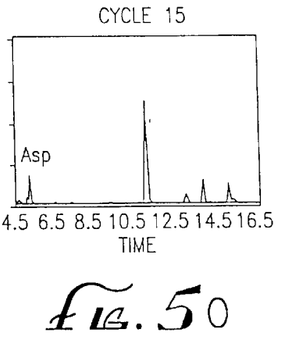
Figure 5P:
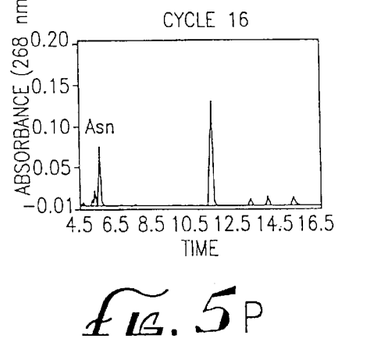
Figure 5Q:
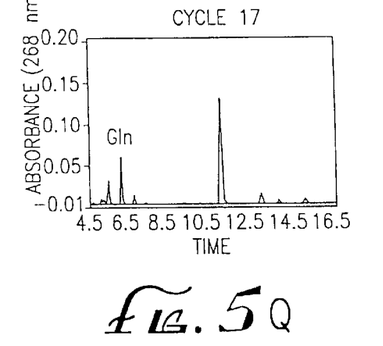
Figure 6A:
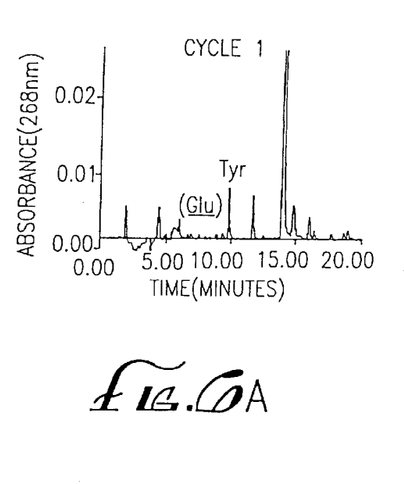
FIGS. 6A–6G show the first seven analytical chromatograms showing the first seven analytes resulting from the sequencing of alpha lactalburnin along with an internal control according to the present invention.
Figure 6B:
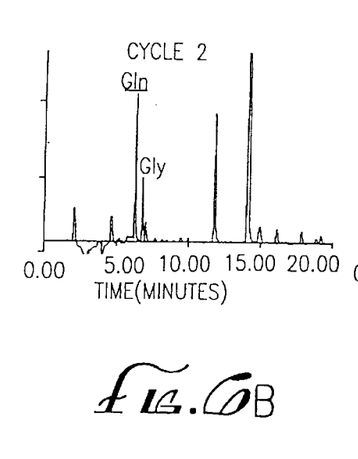
Figure 6C:
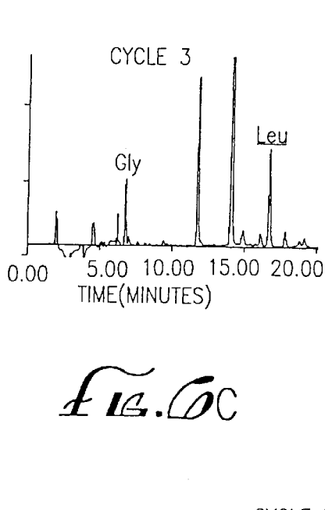
Figure 6D:
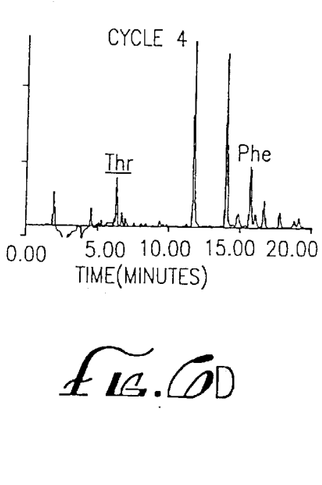
Figure 6E:
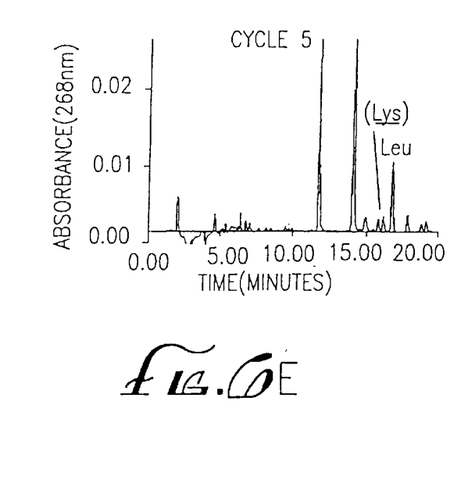
Figure 6F:
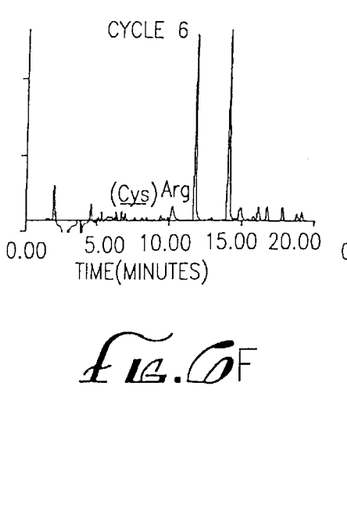
Figure 6G:
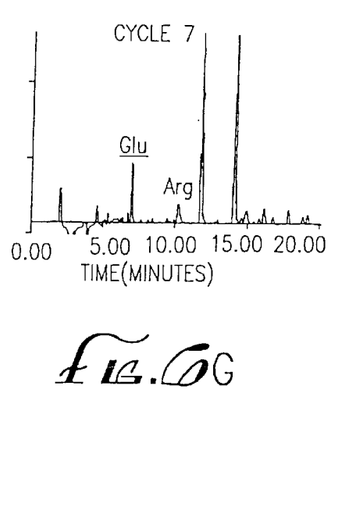

Sequencing chemicals and protocols—Referring to FIG. 4, this invention can be used for both liquid phase and gas phase sequencing. The chemicals and protocols for Edman amino terminal sequencing of a polypeptide are well known in the art and described in Edman and Begg, Eur. J. Biochem., 1:80 (1967). The chemicals and protocols for carboxy terminus sequencing of polypeptides are well known in the art and described in Bailey and Shively, *Techniques in Protein Chemistry II*, Ed., Villafraca, J. Academic Press, N.Y., 1991, p. 115. FIG. 4A shows a flow chart for the steps in amino terminus sequencing and FIG. 4B shows carboxy terminus sequencing of a polypeptide or protein.

Basic method of operation for sequencing of a macromolecule—The sequencing procedure is usually initiated by bonding sample macromolecule to substrates in one or more sequencing packets. A preferred procedure is to perform this operation is a specialized vessel such as a centrifuge cap. Alternatively, packets are placed in the cartridge assembly of the sequencing instrument, and then sample macromolecule along with coupling chemicals are injected into the reaction chamber for in situ bonding of sample macromolecule to substrate. With this method, the cartridge assembly is used both as a reaction chamber for bonding sample macromolecule to the substrate and as a support for the sequencing packets during the degradation chemistry.

Next, sequencing chemicals are injected into the reaction chamber through the inlet to degrade at least one terminal unit referred to as "analyte." This is followed by flushing the reaction chamber with solvent to carry out the analyte. The analyte is then characterized by a technique such as liquid chromatography ("LC"), high performance liquid chromatography ("HPLC"), gas chromatography ("GC"), mass spectroscopy ("MS"), infrared ("IR"), near infrared ("NIR") or ultraviolet ("UV") spectroscopy (with or without being fourier transformed) and nuclear magnetic resonance ("NMR").

More particularly, for example, when Edman sequencing is employed to sequence a polypeptide, the polypeptide is first derivatized by a "coupling reaction" with phenylisothiocyanate ("PITC") by injecting PITC into the reaction chamber to generate a phenylthiocarbamyl (PTC) derivative of the amino terminal amino acid. In the foregoing reaction, a base also needs to be injected along with the PITC to catalyze the reaction. A solvent is then passed through the reaction chamber to remove unreacted reagents and other waste. Next, anhydrous trifluoroacetic ("TFA") is injected into the reaction chamber to cyclize and cleave the amino terminal amino acid of the polypeptide. The cleaved amino acid is then carried out of the reaction chamber as an anilinothiazolinone (ATZ) derivative. The ATZ amino acid is converted to the phenylthiohydantoin (PTH) with aqueous acid. This PTH-amino acid is analyzed by, for example, high performance liquid chromatography. The foregoing protocol is repeated to identify the next amino acid at the amino terminal of the polypeptide. Edman sequencing has a limit of about 100 cycles and is typically used for 30 to 40 cycles.

Some of the advantages of this embodiment of the invention are: (a) use of sequencing packets avoids problems of shrinking, swelling and clogging that occur when sequencing is run in a column packed with organic supports; (b) the sequencing packets are easy to manufacture; (c) the sequencing packets have a high capacity for bonding to macromolecule per unit of volume; and (d) the sequencing packets are chemically inert.

When a control macromolecule (also known as an "internal control" or "standard") is used, it is sequenced simultaneously with the sample macromolecule. The control serves as a basis for confirming that the sequencing operation is functioning properly. The control can also be used for quantitating the amount of sample.

There are four possible results when sequencing with a control:

1. There are two peaks (or lines) in the chromatograph or spectrograph, where one corresponds to an amino acid from the sample and the other corresponds to the expected amino acid from the control. With this result, the assay is functioning properly. There are two peaks (lines) because the terminal unit of the macromolecule and control are different.

2. There is a single peak (or line) of greater area (or height) than that which would be expected from the macromolecule alone. With this result, the assay is functioning properly. There is one peak (or line) because the terminal unit of the sample and control macromolecules are the same.

3. There are no peaks (or lines) which correspond to that expected from the terminal unit in the control. This indicates a malfunction of the sequencing protocol.

4. There is only one peak (or line) having an area (or intensity) equal to that which would be expected for the control only. With this result, the assay is functioning properly and indicates a problem with the sample macromolecule in that only the control is being degraded.

The relative areas (or intensities) of the peaks (or lines) for the control and macromolecule can be used to quantitate the amount of macromolecule.

A preferred control is a synthetic polypeptide that has spaced repeating residues and amino acids that are not naturally occurring or rare. The spaced repeating residues provide for the calculation of reaction efficiency. The non-naturally occurring or rare amino acids minimize overlapping sequences and the resulting confusion of sequencing assignments between sample and control.

Some of the advantages of this embodiment of the invention are: (a) sequencer performance is monitored continually while running sample macromolecule with no need to have separate controls run; (b) the control can be mixed with sample macromolecule in any desired amount; and (c) the control is easily quantitated.

EXAMPLE 1

Sequencing of Dynorphin-A

Container construction—A sheet of polypropylene depth filter was obtained from Gelman Sciences (Ann Arbor, Mich., Part No. 61720) to be used as container material. Arylamine derivatized controlled-pore glass (AA-CPG) beads having an approximately 70 micron diameter were obtained from Sigma Chemical Company (St. Louis, Mo., Part No. 62771) to be used as substrate.

The container was constructed by first cutting two 12 millimeter disks from the sheet of polypropylene depth filter. Thereafter, about 5 milligrams of AA-CPG were piled onto the center of one the disks and the other disk placed on top of the foregoing. The edges of the two disks were held together and sealed with a soldering iron set to about 700° F. The finished container was about 8 millimeters in diameter and 1.5 millimeters in thickness.

Sample Macromolecule—Dynorphin A from Sigma Chemical Company (St. Louis, Mo., Part No. D8147) was selected as the macromolecule to be sequenced. Dynorphin A is a 17 amino acid polypeptide having the following sequence: Tyr-Gly-Gly-Phe-Leu-Arg-Arg-Ile-Arg-Pro-Lys-Leu-Lys-Trp-Asp-Asn-Gln.

Bonding sample macromolecule to substrate—Dynorphin A was bonded to the substrate according to the following protocol. The Dynorphin A was dissolved in a 10% aqueous solution of acetonitrile to a concentration of 700 picomoles per 10 microliters. The container was placed in a 1.5 milliliter plastic centrifuge tube cap. About 15 microliters of 100% acetonitrile was added to the centrifuige tube cap to wet the container to make the polypropylene receptive to aqueous solutions. Before the acetonitrile dried, about 10 microliters of the Dynorphin A sample solution was added to the centrifuge tube cap. The centrifuge tube cap with the container was placed in a heater set at 65° C. and allowed to dry.

Thereafter, the centrifuge tube cap with the container was removed from the heater and 15 microliters of 100% acetonitrile was added to the centrifuge tube cap to rewet the container. Next, 20 microliters of coupling solution (2 milligrams of N-Ethyl-N'-Dimethylaminopropyl carbodiimide ("EDC") in 100 microliters of 0.1 molar 4-morpholine ethanesulfonic acid ("MES") with pH adjusted to 5.0 by sodium hydroxide (MES coupling buffer)) was added to the centrifuge tube cap and allowed to react for about 1 hour. Thereafter, the container was washed thoroughly with deionized water and methanol to remove unbonded Dynorphin A, coupling solution and other contaminants.

Sequencing—The sequencing was performed in a Beckman LF 3000 automated protein sequencer. The LF 3000 employs Edman degradation protein sequencing chemistry. The Dynorphin A bonded by an arylamine to controlled-pore glass was subjected to 17 sequencing cycles.

Results and discussion of results—Referring to FIG. 5, there are 17 analytical chromatograms showing the results of each cycle of the sequencing operation. The chromatograms indicate a correct identification of all 17 amino acids of Dynorphin A. The aspartic acid analyzed in cycle 15 is low. This is expected due to its carboxyl group being involved in coupling to the arylamine on the CPG-AA substrate. The initial yield defined as sample present in the first cycle was 55% of the approximately 700 picomoles of sample loaded onto the substrate. The repetitive yield defined as the efficiency of the Edman degradation protein chemistry was 95.5%. The repetitive yield was measured at the two leucines analyzed in cycles 5 and 12. The initial yield and repetitive yield are comparable to that obtained in sequencing a Dynorphin A according to conventional methods with an arylamine derivatized polyvinylidinedifluoride ("PVDF") disk-shaped membrane as a support.

EXAMPLE 2

Sequencing Of Alpha Lactalbumin Along With A Dynorphin A Control

Construction of Sequencing Packet—Substrate with control was prepared by taking a seventeen residue Dynorphin A polypeptide and coupling it to arylamine-derivatized controlled-pore glass beads ("CPG-AA"). This coupling reaction was performed in a test tube with carbodiimide at pH 5.0 and resulted in the Dynorphin A covalently attaching at its carboxy terminus or at a side chain carboxyl group of aspartic acid at residue 15. The controlled-pore glass beads were washed extensively with water and methanol after coupling to ensure the removal of the coupling reactants and unattached peptide. The sequencing packet was prepared by loading a small amount of the Dynorphin A CPG-AA with controlled pore glass derivatized with diisothiocyanate (CPG-DITC). This resulted in a sample ready sequencing packet containing CPG-DITC and an internal standard.

Bonding sample macromolecule to substrate in sequencing packet—Bovine alpha lactalbumin was selected as a sample for sequencing. 100 picomoles of the protein was loaded onto the CPG-DITC substrate in the sequencing packet. This was done by applying 20 microliter of a stock solution to the sequencing packet. Thereafter, the sequencing packet was dried at 65° C. Coupling was accomplished by applying to the sequencing packet 15 microliters of 20% acetonitrile with 2% triethylamine. The reaction was complete after 30 minutes at 45° C. The sequencing packet was then washed with water and methanol to remove coupling reactants and unattached protein.

Sequencing—Sequencing was performed in a Beckman LF 3000automated protein sequencer. The LF 3000 employed Edman degradation protein sequencing chemistry.

Results and Discussion—Referring to FIG. 6, there are seven analytical chromatographs showing the results of the first seven cycles of the sequencing operation. Each of the chromatograms is labeled to identify the degraded amino acids in that cycle wherein the label for amino acid coming from the alpha lactalbumin sample is underlined and the label for the amino acid coming from the Dynorphin A control is not underlined. There is essentially no signal present for alpha lactalbumin at: (a) cycle 1 because, the amino terminal amino acid remained attached to the CPG-DITC; (b) cycle 5 because the epsilon amino group of lysine permanently attached to the CPG-DITC; and (c) cycle 6 because the native and underivatized cysteine was degraded by the Edman chemistry.

The sequence for the first seven amino acids for the alpha lactalbumin sample and Dynorphin A control is as follows:

Alpha lactalbumin sample: (Glu)-Gln-Leu-Thr-(Lys)-(Cys)-Glu

Dynorphin A control: Tyr-Gly-Gly-Phe-Leu-Arg-Arg

The internal control confirms correct operation of the sequencer in all seven cycles. Accordingly, in cycles 1, 5 and 6 where there was essentially no signal from the sample alpha lactalbumin, the operator knew the sequencing operation was properly functioning based upon a signal from the control Dynorphin A. Had the sample protein been sequenced by itself without any internal control, an operator may have concluded that there was a failure in the sequencing cycles. Further, the operator would have had to wait until the second cycle to determine if the sequencing had started successfully.

Although the present invention has been described in considerable detail with reference to certain preferred versions thereof, other versions are possible. Therefore, the spirit and scope of the appended claims should not be limited to the description of the preferred versions contained herein.

What is claimed is:

1. A method for sequencing a sample macromolecule comprising the steps of:

selecting a sequencing packet comprising a foraminous container containing a plurality of substrates larger than any of the foramen of the container, at least some of the substrates having attached thereto the sample macromolecule, the substrates and the container being insoluble in water;

subjecting the sample macromolecule in the packet to a degradation reaction to cleave a terminal unit from the sample macromolecule, wherein the step of subjecting the sample macromolecule to a degradation reaction is performed within a cartridge assembly having a reaction chamber; and analyzing the cleaved terminal units wherein the sample macromolecule has a non-reactive synthesis functionality.

2. The method of claim 1 wherein the step of selecting a sequencing packet comprises (i) selecting a sequencing packet containing a plurality of substrates derivatized for attaching sample macromolecule thereto, and (ii) passing the sample macromolecule into the container for attachment to the substrates.

3. The method of claim 1 comprising, subsequent to step (b) and before step (c), the additional step of washing the sequencing packet.

4. The method of claim 1 wherein the step of selecting a sequencing packet comprises selecting a disk-shaped packet having a diameter of from about 5 mm to about 15 mm.

5. The method of claim 1 comprising repeating steps (b) and (c) until the sample macromolecule is substantially completely sequenced.

6. The method of claim 1 wherein the sample macromolecule is a polypeptide or protein.

7. A method for sequencing a sample macromolecule simultaneously along with a control macromolecule comprising the steps of:

selecting a sequencing packet comprising a foraminous container containing (i) a first substrate having attached thereto the sample macromolecule, and (ii) a second substrate having attached thereto the control macromolecule, the foramen of the container being smaller than the substrates, the sequence of the control macromolecule being known;

simultaneously subjecting the sample macromolecule and the control macromolecule in the packet to a degradation reaction to cleave at least one terminal unit from both the sample macromolecule and the macromolecule control;

analyzing the cleaved units; and comparing the cleaved units against the known sequence of the control macromolecule to determine if steps (b) and (c) are being performed correctly wherein the sample macromolecule has a non-reactive synthesis functionality.

8. The method of claim 7 wherein the first and second substrates are different from each other.

9. The method of claim 7 wherein the first and second substrates are substantially permanently joined together.

10. The method of claim 7 wherein the first and second substrates are joined to a carrier.

11. The method of claim 7 comprising repeating steps (b) and (c) until the sample macromolecule is substantially completely sequenced.

12. The method of claim 7 wherein the step of selecting a sequencing packet comprises the steps of: (i) selecting a sequencing packet containing the first substrate derivatized for attachment of the sample macromolecule thereto, and also containing the second substrate with the control macromolecule previously attached thereto, and (ii) attaching sample macromolecule to the first substrate in the container.

13. The method of claim 7 wherein the macromolecules are polypeptides or proteins.

14. The method of claim 7 wherein the step of selecting a sequencing packet comprises the steps of (i) selecting a sequencing packet containing the first substrate deriovatized for attachment of the sample macromolecule thereto and the second substrate derivatized for attachment of the control macromolecule thereto, and (ii) attaching sample macromolecule and control macromolecule to the first and second substrates in the control, respectively.

15. The method of claim 14 wherein the sample macromolecule is attached to the first substrate-using a first reaction and the control macromolecule is attached to the second substrate using a second reaction, wherein the first and second reactions are different from each other.

16. Apparatus for sequencing a sample macromolecule comprising:
  (a) a housing having an inlet for introducing degradation reagents into the housing for cleavage of the terminal unit from the sample macromolecules and an outlet for withdrawal of cleaved terminal units from the housing;
  (b) at least one sequencing packet removably contained in the housing, the sequencing packet comprising a foraminous container containing a plurality of substrates larger than any of the foramen of the container, at least some of the substrates having attached therto the sample macromolecule, the substrates and the container being insoluble in water;
  (c) means for placement of sequencing packets into the housing and for removal of sequencing packets from the housing,
  wherein the sample macromolecule contained in the apparatus has a sequence to be sequenced, and wherein the sample macromolecule has non-reactive synthesis functionality.

17. The apparatus of claim 16 comprising a plurality of stacked sequencing packets in the housing.

18. The apparatus of claim 16 comprising a control macromolecule attached to at least some of the substrates, the control macromolecule having a known sequence, the sequences of the control and sample macromolecule being different.

* * * * *